United States Patent [19]

Hsu et al.

[11] Patent Number: 5,648,590
[45] Date of Patent: *Jul. 15, 1997

[54] LIQUID PHASE ISOMERIZATION OF ALKANES

[75] Inventors: Chao-Yang Hsu; Vasant K. Patel, both of Media; David H. Vahlsing, Wynnewood, all of Pa.; James T. Wei, Ridgewood, N.J.; Harry K. Myers, Jr., Cochranville, Pa.

[73] Assignee: Sun Company, Inc. (R&M)

[*] Notice: The term of this patent shall not extend beyond the expiration date of Pat. No. 5,019,671.

[21] Appl. No.: 292,164

[22] Filed: Aug. 17, 1994

Related U.S. Application Data

[63] Continuation of Ser. No. 783,064, Oct. 25, 1991, abandoned, which is a continuation-in-part of Ser. No. 694,735, May 2, 1991, abandoned, which is a continuation of Ser. No. 378,334, Jul. 10, 1989, Pat. No. 5,019,671.

[51] Int. Cl.$^6$ ........................................ C07C 5/13
[52] U.S. Cl. .................... 585/751; 585/734; 585/739; 585/750
[58] Field of Search .................... 585/734, 739, 585/750, 757

[56] References Cited

U.S. PATENT DOCUMENTS

| | | |
|---|---|---|
| 3,878,261 | 4/1975 | Gardner .................... 585/749 |
| 4,025,418 | 5/1977 | Antos . |
| 4,082,651 | 4/1978 | Antos . |
| 4,183,805 | 1/1980 | Antos . |
| 4,197,188 | 4/1980 | Antos . |
| 4,827,076 | 5/1989 | Kokayeff et al. . |
| 4,918,041 | 4/1990 | Hollstein et al. .................... 502/217 |
| 4,956,519 | 9/1990 | Hollstein et al. .................... 585/751 |
| 5,019,671 | 5/1991 | Hsu et al. .................... 585/751 |
| 5,036,035 | 7/1991 | Baba et al. . |

FOREIGN PATENT DOCUMENTS

| | | |
|---|---|---|
| 61-263932 | 11/1986 | Japan . |
| 62-246993 | 10/1987 | Japan . |

*Primary Examiner*—Glenn A. Caldarola
*Assistant Examiner*—Elizabeth D. Wood
*Attorney, Agent, or Firm*—Stephen T. Falk; Q. Todd Dickinson

[57] ABSTRACT

Acyclic hydrocarbons having 4 to 7 carbon atoms per molecule are isomerized in the liquid phase by contact with a solid superacid catalyst comprising sulfated oxide or hydroxide of a metal selected from the group consisting of Group III and Group IV metals, to obtain high octane number blending components for motor fuel and/or valuable chemical and fuel intermediates.

17 Claims, No Drawings

LIQUID PHASE ISOMERIZATION OF ALKANES

CROSS REFERENCE

This application is a continuation of Ser. No. 07/783,064, filed Oct. 25, 1991 and now abandoned, which was a continuation in part of application Ser. No. 07/694,735, filed May 2, 1991 and now abandoned, which was a continuation of application Ser. No. 378,334, filed Jul. 10, 1989, now U.S. Pat. No. 5,019,671, issued May 28, 1991.

FIELD OF THE INVENTION

This invention relates to isomerization of $C_4$ to $C_7$ acyclic hydrocarbons.

BACKGROUND OF THE INVENTION

About 90% of the total butane consumption in the United States is in gasoline manufacture where n-butane is used directly as a blending component, and isobutane is either used for the production of high octane alkylate or for the production of isobutylene to make tert-butyl ether. Chemical uses account for another 6–8% of the total butanes. Due to the recent increased demand for high octane gasoline and the federally regulated reduction of gasoline vapor pressure, there is the need to have a process that can effectively convert normal butane to the higher octane rated isobutane, to ultimately increase the production of light octane blending components.

Current butane isomerization processes, using either aluminum chloride or chlorinated platinum on alumina or zeolite catalysts, require high operating temperature and use hydrogen as a cracking suppresser. Thus, the commercial processes could only operate in the vapor phase. We have discovered a liquid phase process for the isomerization of normal butane to isobutane. The liquid phase operation provides engineering design and operating cost advantages over conventional vapor phase processes. In the process design area, savings are available due to reduced size of liquid containing lines, reduction of pump energy requirements and elimination of the compressors needed in a vapor phase process to overcome pressure drop through the process, and use of lower cost equipment for heat input by avoiding vaporization of the butane feed. These equipment simplifications also result in less utility requirement for the drivers for pumps and compressors, and eliminate the need of fired heat for vaporization and of cooling water for condensing. In addition, the liquid phase operation also provides other benefits such as lower catalyst deactivation rates than those in the vapor phase operations.

Pentane isomerization is also of commercial interest and is presently carried out with similar platinum on zeolite catalyst and in the vapor phase. The design and cost advantages for a liquid phase pentane isomerization are similar to those described above for butane liquid phase isomerization. $C_6$ and $C_7$ alkanes may also be isomerized according to the invention.

The possibility of liquid phase alkane isomerization is enhanced by the recent discovery of a very active solid superacid catalyst system which is disclosed and claimed in pending application of Hollstein, Wei and Hsu, Ser. No. 247,225 filed Sep. 21, 1988, now U.S. Pat. No. 4,918,041. However the invention is applicable to superacid catalysts generally which have activity for alkane isomerization.

SUMMARY OF THE INVENTION

According to the present invention, a feedstock is isomerized by contacting the same in liquid phase with a solid superacid catalyst at a temperature in the range from 0° to 250° C. and a pressure in the range from 1 to 75 atmospheres. Combinations of temperature and pressure are used which cause the reaction mixture to be in liquid phase.

According to the present invention, a feedstock is isomerized by contacting the same in liquid phase with a solid superacid catalyst at a temperature in the range from 0° to 250° C. and a pressure in the range from 1 to 75 atmospheres. Combinations of temperature and pressure are used which cause the reaction mixture to be in liquid phase. The combinations that produce liquid phase conditions depend of course upon the molecular weight of the feedstock. Superacids are compounds which have acidity stronger than concentrated sulfuric acid ($H_o<-12$). Solid superacids are superacids which are solid at normal atmospheric temperatures and pressures.

DETAILED DESCRIPTION

Preferred superacids for use according to the invention are the solid acids which have acidities stronger than 100% $H_2SO_4$ (i.e. $H_o<12$). Examples of the solid superacids are sulfated zirconia, sulfated titania, sulfated iron oxide, sulfated zirconia containing one or more metals, sulfated titania containing one or more metals, halogenated alumina (such as fluorinated $Al_2O_3$, etc.), and a mixture of tungstate oxide and zirconia calcined at 800° C., etc. Other types of solid superacids are strong Lewis acids such as $SbF_5$, $SbCl_5$, $SbF_5$/HF, on a solid support such as silica, alumina or zirconia or combinations thereof.

Particularly preferred catalyst for use in the process according to the invention comprises a sulfated and calcined solid mixture of (1) oxide or hydroxide of metal from a first class consisting of Group III and Group IV, (2) oxide or hydroxide from a second class consisting of Group V, Group VI or Group VIII metal and (3) oxide or hydroxide of Group VIII metal. The weight ratio of metal from the second class to Group VIII metal is in the range from 0.1:1 to 2.0:1, preferable 0.2:1 to 1.0:1. The catalyst preferably contains a major amount of oxide or hydroxide of metal from the first class and a minor amount, preferably in the range from 0.02 to 15.0 weight percent, more preferably 0.1 to 4.5 weight percent, of total metal from the second class and Group VIII metal.

The carrier or support for the catalyst according to the invention is an oxide or hydroxide of a Group III or Group IV element. Examples of such suitable elements are aluminum, gallium, indium, thallium, titanium, zirconium, hafnium, silicon, germanium, tin and lead. Preferred are silicon, aluminum, zirconium and mixtures of two or more thereof.

Metals from Groups V, VI or VII which can be used according to the invention include arsenic, antimony, bismuth, vanadium, niobium, tantalum, selenium, tellurium, chromium, molybdenum, tungsten, manganese and rhenium and mixtures of two or more thereof.

Metals from Group VIII which can be used according to the invention include iron, cobalt, nickel, ruthenium, rhodium, palladium, osmium, iridium and platinum and mixtures of two or more thereof.

The catalysts according to the invention may be prepared for example by impregnating a support of a Group III or Group IV metal oxide or hydroxide with an aqueous solution containing compounds of Group VII and Group VIII metals. Alternatively, the support can be impregnated separately with a solution of a Group VII metal compound and a solution of a Group VIII metal compound.

The catalysts according to the invention may also be prepared by co-precipitation of solid hydroxides of (1) Group III or Group IV metals, (2) Group V, Group VI or Group VII metals and (3) Group VIII metals, from aqueous solutions containing compounds of such metals. In such method, the amount of the Group VIII metal hydroxide is typically in the range from 0.01 to 10.0 percent by weight of the total precipitated hydroxide. Mixtures of Group III and Group IV metal oxides or hydroxides, or of two or more from among Group V, Group VI and Group VII metal oxides or hydroxides, may be employed.

Solutions of metal compounds which can be used in the preparation of catalysts according to the invention, by impregnation or co-precipitation, are known in the art. For example, aqueous solution of chloroplatinic acid or tetra-ammine-platinum complex can be used to incorporate platinum in the catalyst. Nitrates of iron and of manganese can be used for example to incorporate those metals in the catalyst. Solutions of zirconium oxychloride or of zirconyl nitrate can be used, for example, to prepare a zirconium support for the catalyst according to the invention. Various other solutions can be employed as needed.

Sulfate ion may be supplied to the catalyst according to the invention by treatment of the solid catalyst with sulfuric acid, for example 0.01–10 N sulfuric acid, preferably 0.1–5 N sulfuric acid. Other compounds such as ammonium sulfate capable of providing sulfate ion can be employed. Compounds such as hydrogen sulfide or sulfur dioxide or mercaptans, capable of forming sulfate ions upon calcining, can also be employed. Preferred catalysts for use according to the invention are those which have been sulfated with ammonium sulfate.

The catalysts according to the invention contain substantial amounts of sulfate ion, preferably in amount of 0.5 to 20 weight percent based on total catalyst, and more preferably 5 to 15 weight percent.

The catalysts according to the invention are calcined at a temperature which is preferably in the range from 450°–800° C., more preferably 550°–700° C., and for a period of time in the range from 30 minutes to 30 hours. Combinations of temperature and time can be chosen in order to provide a desired degree of conversion. For example, calcining at 550° C. for 12 hours provides about the same initial conversion of n-butane to isobutane as calcining at 575° C. for 4 hours.

The process according to the invention is used to isomerize normal alkanes having four to seven carbon atoms, namely butane, pentane, hexane and heptane, to convert the straight chain hydrocarbons into branched chain hydrocarbons having higher octane number for use as motor fuel or, as in the case of butane, having enhanced value as an intermediate for such products as tertiarybutyl alcohol and high octane alkylates.

The isomerization is carried out by contacting the hydrocarbon feed in liquid phase with the solid catalyst at temperatures in the range from 0° C. to 250° C., preferably in the range from 20° to 175° C. and at pressure in the range from 1 to 75 atmospheres, more preferably 10 to 50 atmospheres. The isomerization may be conducted either in the presence or absence of hydrogen. If conducted in the presence of hydrogen, the mole ratio of hydrogen to hydrocarbon is preferably in the range from 0.1:1 to 10:1. Inert gas such as nitrogen, helium or argon may be employed. Preferably, the isomerization is conducted in the absence of added gas. If added gas is employed, the amounts added are sufficiently small to avoid vaporization of the liquid hydrocarbon feed.

Generally, a temperature is used in the isomerization which is sufficiently high to obtain a desired rate of reaction, but not so high as to result in vaporization and consequently more rapid deactivation of catalyst.

EXAMPLES

The following examples illustrate the invention:

Example 1

Liquid phase isomerization of n-butane in a Parr 300 ml. constant stirring reactor was conducted by charging 2.5 g of catalyst and 50 g of n-butane, and under the reaction conditions of 200 psig and 50° C. The reaction was monitored by taking liquid samples hourly and subjected to GC analyses. The results are shown in Table I.

Example 2

Similar reaction procedures and conditions as described in Example 1 were used for this reaction excepting that the amount of catalyst was increased to 5.0 g. The results are shown in Table II.

Example 3

A mixed feed of n-butane and nitrogen at a molar ratio of 2:1 was flowed downward through a fixed bed reactor containing 5.0 ml. of catalyst. The reaction conditions were 50° C. and 293 psig. Butane vapor pressure at 50° C. is 57.3 psig, and vapor pressure calculations indicate that this is a liquid phase reaction. GC analyses of the reaction products indicated that the yield of i-butane was 11% when LHSV (liquid hourly space velocity)=0.44 and i-butane yield was 5.1% when LHSV=0.88. The results are shown in Table III.

Example 4

Liquid n-butane was pumped upward at a rate of 50 ml. per hour through a fixed bed reactor containing 50 ml. of catalyst and under 220 psig pressure. The reactor temperature was slowly increased to 75° C. and the reaction was run at this temperature for about 70 hours. The reaction samples were taken for on-line GC analyses every hour. The GC results as shown in Table IV indicate that this reaction gives an average of 35% yield of i-butane at 75° C.

Example 5

For the purpose of comparison, the same catalyst and reaction conditions as described in Example 4 were used excepting that the reaction pressure was maintained at 100 psig to keep the reaction in the vapor phase. The results obtained from GC analyses as shown in Table V indicated that the vapor phase reaction gave an average of 20% yield of i-butane.

Example 6

Liquid phase isomerization of n-pentane to i-pentane was demonstrated using an up-flow reactor and under the conditions of 92 psig and LHSV=1.2. The results are shown in Table VI.

TABLE I

Liquid Phase Isomerization of n-Butane in a Constant Stirring Reactor

|  | 1.0 Hr | 2.0 Hr | 3.0 Hr | 4.0 Hr |
|---|---|---|---|---|
| Products (mmol) | | | | |
| $C_2$ | 0.01 | 0.01 | 0.01 | 0 |
| $C_3$ | 1.00 | 0.87 | 0.94 | 0.95 |
| $i-C_4$ | 4.92 | 5.69 | 6.00 | 6.42 |
| $i-C_5$ | 0.73 | 0.80 | 0.78 | 0.80 |
| $n-C_5$ | 0.04 | 0.06 | 0.06 | 0.06 |
| $C_5+$ | 0.13 | 0.36 | 0.25 | 0.25 |
| Total (mmol) | 6.83 | 7.79 | 8.04 | 8.48 |
| Mmol/hr/g-Cat | | | | |
| Total Prod. | 2.72 | 1.56 | 1.07 | 0.85 |
| $i-C_4$ | 0.38 | 1.14 | 0.80 | 0.64 |
| Sel. (% $i-C_4$) | 66.3 | 68.1 | 69.6 | 70.5 |

TABLE II

Liquid Phase Isomerization of n-Butane in a Constant Stirring Reactor

|  | 1.0 Hr | 2.0 Hr | 3.0 Hr | 4.0 Hr |
|---|---|---|---|---|
| Products (mmol) | | | | |
| $C_2$ | 0.02 | 0.02 | 0.01 | 0.01 |
| $C_3$ | 1.12 | 1.30 | 1.06 | 1.10 |
| $i-C_4$ | 8.49 | 10.1 | 11.3 | 11.8 |
| $i-C_5$ | 0.84 | 0.83 | 0.90 | 0.89 |
| $n-C_5$ | 0.09 | 0.10 | 0.10 | 0.11 |
| $C_5+$ | 0.10 | 0.18 | 0.21 | 0.24 |
| Total (mmol) | 10.66 | 12.54 | 13.54 | 14.17 |
| Mmol/hr/g-Cat | | | | |
| Total Prod. | 2.13 | 1.26 | 0.90 | 0.71 |
| $i-C_4$ | 1.70 | 1.01 | 0.75 | 0.59 |
| Sel. (% $i-C_4$) | 75.6 | 76.5 | 79.7 | 80.7 |

TABLE III

Liquid Phase Isomerization of n-Butane in a Fixed Bed Down Flow Reactor
(Reaction conditions: 50° C., 293 psig.)
(Feed composition: butane/nitrogen = 2/1)

| Reaction Time (hr) | 14.0 | 16.0 | 18.0 | 20.0 | 23.0 | 24.0 | 25.0 | 26.0 |
|---|---|---|---|---|---|---|---|---|
| LHSV (l/Hr) | 0.44 | 0.44 | 0.44 | 0.44 | 0.88 | 0.88 | 0.88 | 0.88 |
| GC analyses (Weight %) | | | | | | | | |
| $C_3$ | 0.136 | 0.090 | 0.134 | 0.133 | 0.036 | 0.030 | 0.032 | 0.028 |
| $i-C_4$ | 12.28 | 11.78 | 13.01 | 11.76 | 5.670 | 5.407 | 5.125 | 4.128 |
| $n-C_4$ | 87.46 | 88.06 | 86.79 | 88.02 | 91.36 | 94.45 | 94.57 | 91.96 |
| $i-C_5$ | 0.103 | 0.010 | 0.011 | 0.080 | 2.302 | 0.103 | 0.263 | 2.348 |
| $n-C_5$ | 0.020 | 0.010 | 0.011 | 0.011 | 0.623 | 0.004 | 0.003 | 0.935 |

TABLE IV

Liquid Phase Isomerization of Butane Using an Up Flow Fixed Reactor at Various Temperatures
(Pressure: 100–150 psig., LHSV = 1.0)

| Reaction Time (Hr) | 10 | 15 | 20 | 25 | 30 | 35 | 40 | 45 |
|---|---|---|---|---|---|---|---|---|
| Reaction Temp. (°C.) | 50 | 50 | 50 | 60 | 60 | 60 | 60 | 60 |
| Reaction Press. (Psig) | 100 | 100 | 100 | 130 | 135 | 135 | 135 | 135 |
| GC Analyses (Weight %) | | | | | | | | |
| $C_3$ | 0.45 | 0.44 | 0.41 | 0.55 | 0.56 | 0.56 | 0.55 | 0.54 |
| $i-C_4$ | 18.30 | 17.59 | 16.09 | 23.16 | 23.95 | 22.92 | 22.09 | 21.51 |
| $n-C_4$ | 80.84 | 81.63 | 83.20 | 75.79 | 74.95 | 76.03 | 76.89 | 77.49 |
| $i-C_5$ | 0.33 | 0.28 | 0.25 | 0.41 | 0.44 | 0.40 | 0.39 | 0.37 |
| $n-C_5$ | 0.06 | 0.05 | 0.05 | 0.08 | 0.09 | 0.08 | 0.08 | 0.07 |
| Reaction Time (Hr) | 50 | 55 | 60 | 70 | 80 | 90 | 100 | 140 |

TABLE IV-continued

Liquid Phase Isomerization of Butane
Using an Up Flow Fixed Reactor at Various Temperatures
(Pressure: 100–150 psig., LHSV = 1.0)

| Reaction Temp. (°C.) | 65 | 70 | 70 | 70 | 74 | 76 | 76 | 76 |
|---|---|---|---|---|---|---|---|---|
| Reaction Press. (Psig) | 135 | 135 | 128 | 128 | 150 | 150 | 150 | 150 |
| GC Analyses (Weight %) | | | | | | | | |
| $C_3$ | 0.70 | 0.67 | 0.90 | 0.91 | 1.17 | 1.11 | 1.08 | 0.99 |
| $i\text{-}C_4$ | 27.63 | 26.87 | 33.83 | 32.71 | 29.17 | 38.34 | 37.74 | 35.92 |
| $n\text{-}C_4$ | 70.99 | 71.79 | 64.26 | 65.47 | 57.50 | 58.45 | 58.92 | 6.193 |
| $i\text{-}C_5$ | 0.55 | 0.54 | 0.81 | 0.73 | 1.09 | 1.07 | 1.02 | 0.93 |
| $n\text{-}C_5$ | 0.11 | 0.11 | 0.17 | 0.15 | 0.23 | 0.23 | 0.23 | 0.20 |

TABLE V

Vapor Phase Isomerization of Butane
Using a Fixed Bed Reactor at Various Temperatures

| Reaction Time (Hr) | 15 | 25 | 35 | 45 | 56 | 66 | 76 | 86 |
|---|---|---|---|---|---|---|---|---|
| Reaction Temp. (°C.) | 75 | 75 | 85 | 85 | 85 | 85 | 85 | 85 |
| Reaction Press. (psig) | 100 | 100 | 100 | 100 | 100 | 100 | 100 | 100 |
| GC Analyses (Weight %) | | | | | | | | |
| $C_3$ | 0.43 | 0.46 | 0.77 | 0.68 | 0.61 | 0.57 | 0.54 | 0.49 |
| $i\text{-}C_4$ | 17.08 | 16.03 | 28.22 | 25.16 | 22.56 | 20.84 | 19.58 | 18.18 |
| $n\text{-}C_4$ | 82.04 | 83.16 | 70.15 | 73.50 | 76.22 | 78.06 | 80.86 | 68.35 |
| $i\text{-}C_5$ | 0.37 | 0.29 | 0.70 | 0.53 | 0.49 | 0.44 | 0.40 | 0.38 |
| $n\text{-}C_5$ | 0.07 | 0.06 | 0.13 | 0.10 | 0.09 | 0.08 | 0.07 | 0.07 |

TABLE VI

Liquid Phase Isomerization of n-Pentane
In an Up Flow Fixed Bed Reactor at Various Temperatures
(Reaction conditions: Press. = 92 psig., LHSV - 1.2)

| Reaction Time (Min) | 37 | 67 | 97 | 127 | 157 | 187 | 217 | 247 | 277 | 307 | 337 |
|---|---|---|---|---|---|---|---|---|---|---|---|
| Reaction Temp. (°C.) | 19 | 19 | 20 | 28 | 36 | 44 | 52 | 60 | 68 | 74 | 75 |
| GC Analyses (Weight %) | | | | | | | | | | | |
| $i\text{-}C_4$ | 0.07 | 0.23 | 0.35 | 0.28 | 0.27 | 0.44 | 0.73 | 1.64 | 1.70 | 2.76 | 2.21 |
| $i\text{-}C_5$ | 5.70 | 9.95 | 12.04 | 12.12 | 13.22 | 18.35 | 23.7 | 29.32 | 30.44 | 35.04 | 35.22 |
| $n\text{-}C_5$ | 93.80 | 89.20 | 86.80 | 86.90 | 85.60 | 78.98 | 73.96 | 66.66 | 65.28 | 57.82 | 59.16 |
| $2,2\text{-}DMC_4$ | 0.03 | 0.08 | 0.11 | 0.09 | 0.09 | 0.13 | 0.20 | 0.39 | 0.39 | 0.55 | 0.44 |
| $2,3\text{-}DMC_4$ | 0.01 | 0.01 | 0.01 | 0.01 | 0.02 | 0.02 | 0.05 | 0.11 | 0.14 | 0.24 | 0.21 |
| $2\text{-}MC_6$ | 0.04 | 0.13 | 0.21 | 0.17 | 0.19 | 0.28 | 0.45 | 0.94 | 1.03 | 1.60 | 1.45 |
| $3\text{-}MC_5$ | 0.03 | 0.06 | 0.09 | 0.08 | 0.09 | 0.13 | 0.20 | 0.41 | 0.46 | 0.71 | 0.64 |
| $n\text{-}C_6$ | 0.01 | 0.01 | 0.02 | 0.01 | 0.02 | 0.03 | 0.05 | 0.11 | 0.12 | 0.20 | 0.18 |

The catalyst used in Examples 1 to 6 was a solid superacid prepared as follows: Suitable amounts of zirconyl nitrate and ferric nitrate and manganese nitrate are dissolved in de-ionized water to make 1.0 liter of solution (A) of concentrations as hereinafter indicated. 130 grams of concentrated ammonium hydroxide are diluted with sufficient de-ionized water to make 1.0 liter of solution (B). 500 milliliters of de-ionized water are added to a 5 liter Morton flask. Solution (A) and solution (B) are added concurrently from two addition funnels to the Morton flask slowly with rapid stirring. The pH of the resulting reaction mixture is kept at about 7.0. The reaction slurry is filtered and the filter cake is washed with de-ionized water several times until the filtrate is nitrate free. The damp cake is applied to perforated plates, placed in a tray and dried overnight at 150° C. The pellets are removed from the tray, transferred to a porcelain dish and calcined in an oven at 500° C. for 4.0 hours. The calcined pellets are added slowly to a beaker containing 1.0 normal sulfuric acid solution at room temperature. The amount of sulfuric acid is determined by the following ratio of 15 milliliters of 1.0 normal sulfuric acid per gram of pellet. The sulfuric acid solution is decanted after the pellets are soaked for 2.0 hours. The pellets are calcined again at 500° C. for 4 hours.

Similar results to the above are obtained using superacid catalysts such as solid sulfated zirconia or $SbF_5$ in place of the catalysts used in the above examples. The preparation of such catalysts is known in the art.

The invention claimed is:

1. The method of isomerizing a feedstock having 4 to 7 carbon atoms per molecule which comprises contacting said feedstock in liquid phase with a solid superacid catalyst comprising sulfated oxide or hydroxide of a metal selected from the group consisting of Group III and Group IV metals, wherein said contacting is carried out at a temperature and pressure suitable for isomerizing said feedstock.

2. The method of claim 1 wherein said metal comprises a metal selected from the group consisting of silicon, aluminum, zirconium, titanium and combinations thereof.

3. The method of claim 2 wherein said metal comprises zirconium.

4. The method of claim 1 wherein said catalyst further comprises oxide or hydroxide of one or more second metals selected from the group consisting of Group V, VI, VII and VIII metals.

5. The method of claim 4 wherein said second metal is selected from the group consisting Group VIII metals.

6. The method of claim 5 wherein said second metal comprises iron.

7. The method of claim 5 wherein said second metal comprises cobalt.

8. The method of claim 4 wherein said second metal is selected from the group consisting of Group VII metals.

9. The method of claim 8 wherein said second metal comprises manganese.

10. The method of claim 4 wherein said second metal comprises iron and manganese.

11. The method of claim 1 wherein said temperature is in the range from 0° to 250° C. and said pressure is in the range from 1 to 75 atmospheres.

12. The method of claim 11 wherein said temperature is in the range from 20° to 175° C. and said pressure is in the range from 10 to 50 atmospheres.

13. The method of claim 1 wherein said catalyst contains 5 to 15 weight percent of sulfate ion.

14. The method of claim 1 wherein said catalyst has been sulfated with ammonium sulfate.

15. The method of claim 1 wherein said contacting occurs in the absence of added gas.

16. The method of claim 1 wherein said feedstock comprises normal alkanes having 4 to 7 carbon atoms per molecule.

17. The method of claim 16 wherein said feedstock comprises n-butane.

* * * * *